United States Patent [19]
Holden et al.

[11] Patent Number: 4,765,193
[45] Date of Patent: Aug. 23, 1988

[54] OXYGEN SYSTEM ANALYZER

[75] Inventors: Ronald D. Holden; John B. Tedor; Andrew O. Bergquist; David S. Moran; Mike Eiserer, all of San Antonio, Tex.

[73] Assignee: The United States of America as represented by the Secretary of the Air Force, Washington, D.C.

[21] Appl. No.: 59,641

[22] Filed: Jun. 8, 1987

[51] Int. Cl.$^4$ .................... G01M 19/00; G01D 21/02
[52] U.S. Cl. ...................................... 73/865.9; 73/23; 73/198
[58] Field of Search ................ 73/865.9, 23, 198, 714; 98/1.5

[56] References Cited

U.S. PATENT DOCUMENTS

| | | | |
|---|---|---|---|
| 3,500,827 | 3/1970 | Paine | 128/142.5 |
| 3,587,438 | 6/1971 | Foster et al. | 98/1.5 |
| 3,720,501 | 3/1973 | Cramer et al. | 23/281 |
| 4,240,798 | 12/1980 | Wendelin et al. | 23/230 A |
| 4,462,246 | 7/1984 | Advoni et al. | 73/23 |
| 4,553,474 | 11/1985 | Wong et al. | 98/1.5 |
| 4,562,723 | 1/1986 | Hubner | 73/23 |
| 4,584,960 | 4/1986 | Colling, Jr. | 114/333 |

Primary Examiner—Tom Noland
Attorney, Agent, or Firm—Donald J. Singer; Thomas L. Kundert; Bernard E. Franz

[57] ABSTRACT

Test and man-rating of an oxygen generation system required analytical methods for evaluating system performance both in the laboratory and on the aircraft. The Oxygen System Analyzer is capable of monitoring four performance variables which include: (1) system gas flow rate, (2) product oxygen concentration, (3) system outlet pressure, and (4) aircraft cabin pressure. The analyzer is a portable tester designed to be used on a frequent basis to ascertain system performance and assure reliability and safety. The device may be used either in preflight system checkout mode or to assess in-flight performance characteristics and compliance with design specifications. The analyzer is packaged in a flight worthy case (20×13×8.5 inches, 31 pounds) and operates from a 12 volt rechargeable power system for 8-10 hours. Data is handlogged from digital panel meters. The analyzer is also capable of being adapted to assess system performance for other types of oxygen systems whether onboard aircraft, at sea or at land-based locations.

4 Claims, 6 Drawing Sheets

OXYGEN SYSTEM ANALYZER

RIGHTS OF THE GOVERNMENT

The invention described herein may be manufactured and used by or for the Government of the United States for all governmental purposes without the payment of any royalty.

BACKGROUND OF THE INVENTION

The present invention relates generally to a portable oxygen system analyzer, particularly for evaluating the performance of an oxygen system in a vehicle such as an aircraft.

A function of aerospace research is to find solutions for a host of problems that plague pilots and aircrew. This involves test and evaluation (T&E) and human performance evaluation (manrating) of new and proposed items of life support gear for both air and ground support crews.

One of the items of aircrew life support gear is an on board oxygen generation system, one type being a Molecular Sieve Oxygen Generation System (MSOGS). (An accepted generic term for molecular sieve oxygen systems is On Board Oxygen Generation System or OBOGS). A system that has undergone T&E and manrating is the MSOGS for the B1-B bomber. The entire MSOGS including concentrator, valves, regulators, backup oxygen supply, switches, hoses and supply tubing configured exactly as in the airplane airframe was installed in a large altitude chamber for formal evaluation. The test configuration was as close to the actual aircraft design as the engineers could make it. Multiple operational tests were then conducted to determine the performance characteristics of the MSOGS as it would appear in the actual B1-B installation.

As an adjunct to the T&E of the MSOGS in the altitude chamber mockup configuration it was decided that an alternate method of evaluating system performance after aircraft installation would be beneficial.

United States patents of interest include U.S. Pat. No. 3,500,827 to O'Reilly, which teaches a portable life support system for use with a space garment. Means are provided for circulating both oxygen and a cooling liguid. U.S. Pat. No. 3,587,438 to Foster teaches a control system for maintaining the gas mixture including oxygen under pressure within a chamber. The system has the capability of preferentially supplying oxygen from a sourc to the chamber whenever the oxygen partial pressure is below a predetermined level. U.S. Pat. No. 3,720,501 to Cramer teaches a system enriching the ambient air with oxygen as a result of the release of oxygen from barium oxide in a vacuum. U.S. Pat. No. 4,240,798 to Wendelin teaches a method of reducing ozone in an aircraft cabin by detecting the ozone level and then releasing a source of nitric oxide to reduce ozone if it has reached an undesirable level. U.S. Pat. No. 4,553,474 to Wong teaches a method to control air pressure during periods of ground, takeoff and landing. U.S. Pat. No. 4,584 960 to Colling teaches a control system for undersea vehicles as well as aircraft. The system controls cabin pressurization as a result of sensing atmospheric conditions.

SUMMARY OF THE INVENTION

An objective of the invention is to fill an operational test void by providing a portable oxygen system analyzer (tester) that is reliable, easy to operate and provides a quick functional check concerning the most important performance parameters of an oxygen generation system.

The oxygen system analyzer according to the invention is an in-flight test kit for measuring breathing gas pressure, oxygen concentration and delivered flow relative to and cabin pressure for oxygen systems installed on board an aircraft. The components which make up the system are pressure transducers, flow meter, oxygen sensor, digital voltage meters, battery pack, switches, fuses and valves. In operation, the test kit is calibrated to a standard for each parameter under test. The on board environmental parameters are then tested individually to ascertain whether they fall within acceptable standard ranges. The OBOGS would be removed and replaced by another unit if it did not conform. The removed unit would then be sent for bench check at an appropriate depot for possible overhaul.

The unit can be used as a ground level preflight tester or can be flown to obtain actual in-flight performance data from any On Board Oxygen Generation System.

DETAILED DESCRIPTION

Test and man-rating of the B-1B Molecular Sieve Oxygen Generation System (MSOGS) required analytical methods for evaluating system performance both in the laboratory and on the aircraft. In conjunction with the performance testing and man-rating of the MSOGS in USAFSAM laboratories a portable oxygen system analyzer was developed. The analyzer is a portable tester designed to be used on a frequent basis to ascertain system performance and assure reliability and safety. The device may be used in either a preflight system checkout mode or to assess in-flight performance characteristics and compliance with design specifications. The analyzer is packaged in a flight worthy case (20×13×8.5 inches, 31 pounds) and operates from a 12 volt rechargeable power system for 8-10 hours. The analyzer is also quite capable of being adapted to assess system performance for other types of oxygen systems whether on board aircraft, at sea, or at land-based locations. (The Navy has plans to use similar molecular sieve systems on board aircraft carriers, etc.).

Figure 1:
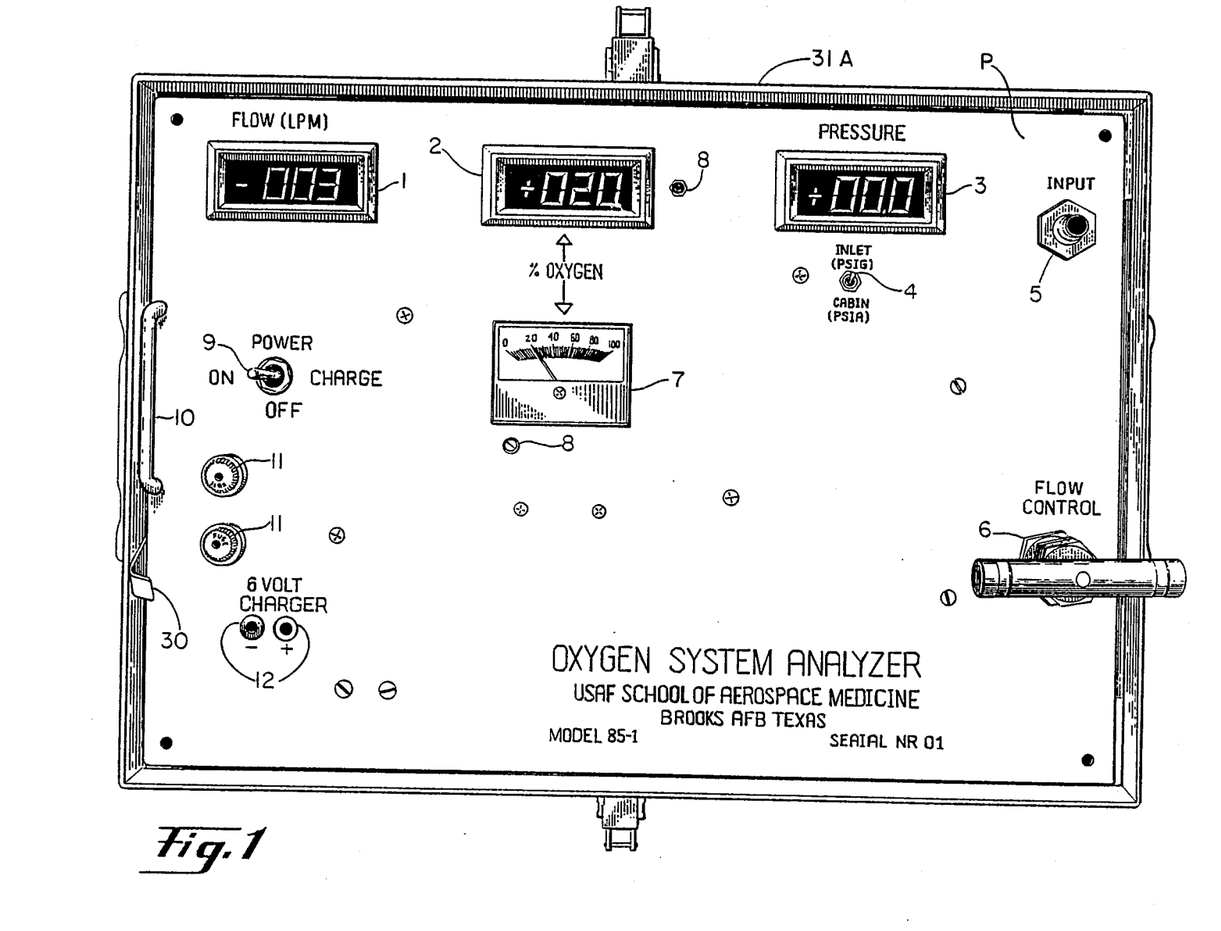
FIG. 1 is a view of the analyzer face plate.
Figure 2:
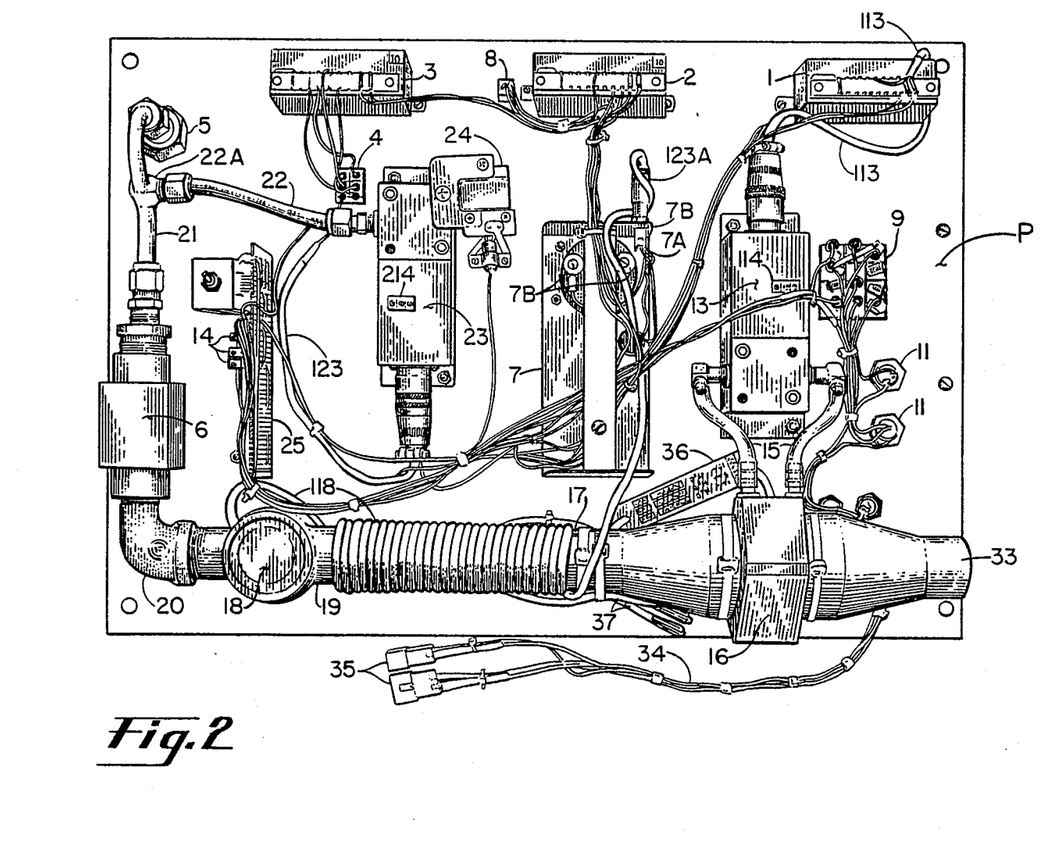
FIG. 2 is a view of the back or underside of the face plate.
Figure 3:
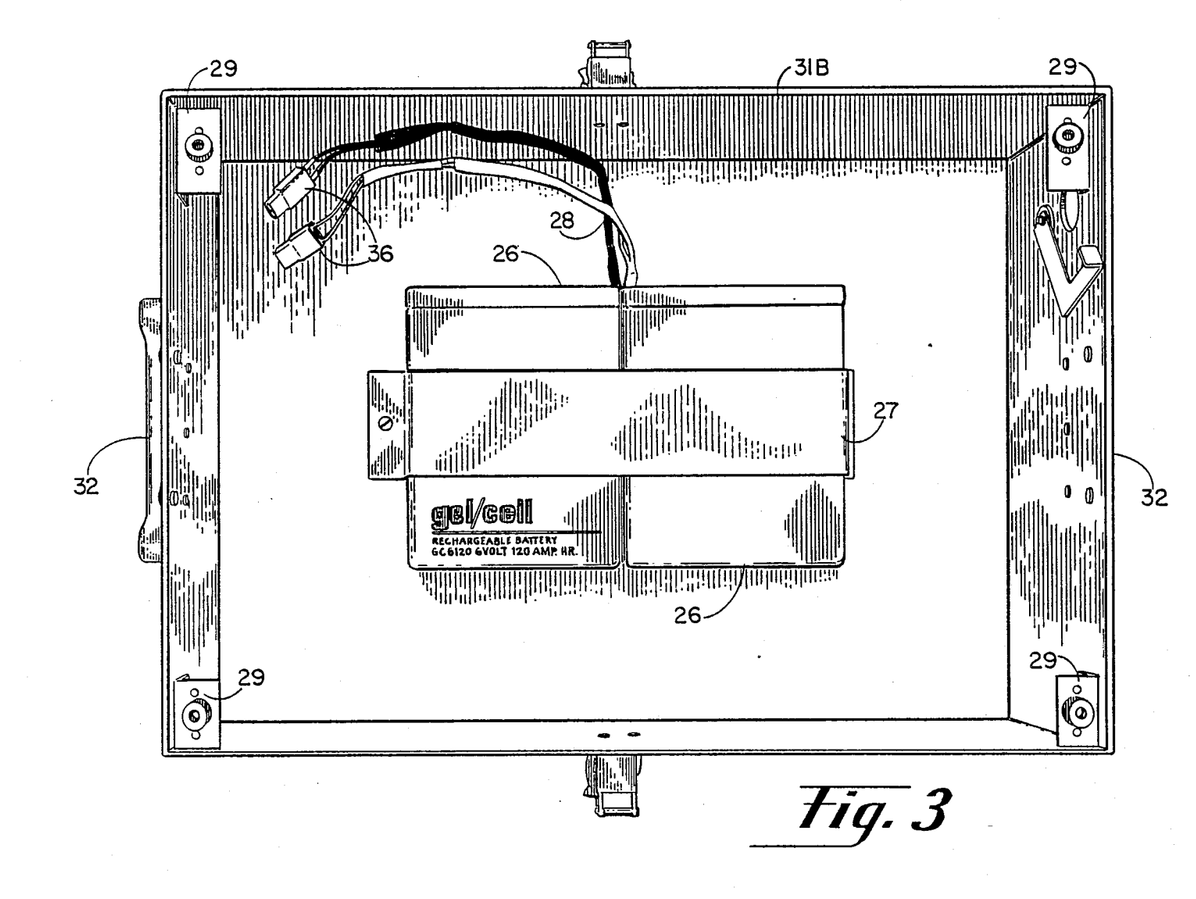
FIG. 3 is a view of the battery pack and case (color photographs corresponding to FIGS. 1, 2 and 3 are enclosed with this patent application as filed)

Most of the parts of the analyzer are mounted on a face plate shown in FIGS. 1 and 2. FIG. 1 is a view of the face plate P mounted in one section 31A of the case. FIG. 2 is a view of the back or underside of the faceplate P removed from the case, showing the location of the principal parts of the unit, with the electrical wiring omitted for clarity. FIG. 3 is a view of the inside of another section 31B of the case in which the battery pack 26—26' is mounted with a clamp 27. FIGS. 1, 2 and 3 correspond to the three enclosed color photographs. The two sections 31A & 31B of the case clamp together for carrying the analyzer. For using the analyzer, the case is opened, and wiring connectors 35 from the faceplate section and connectors 36 of the battery pack section are plugged together. The faceplate section 31A is then fastened inside of the other section 31B with the face up as shown in FIG. 1. A product gas supply hose (not shown) is connected from the outlet of the oxygen generation system to the inlet 5 on the faceplate.

The portable oxygen system analyzer evaluates the four following performance variables, (a) product gas flow, (b) product gas pressure, (c) product gas oxygen concentration and (d) aircraft cabin pressure. The MSOGS or any OBOGS type system delivers oxygen concentrations that are affected by (a) inlet air pressure, (b) user flow demand, (c) cabin/aircraft pressure differential, and (d) molecular sieve bed size. To adequately assess the performance of an OBOGS the four variables monitored by the portable analyzer should be checked in flight during actual missions.

Figure 4:
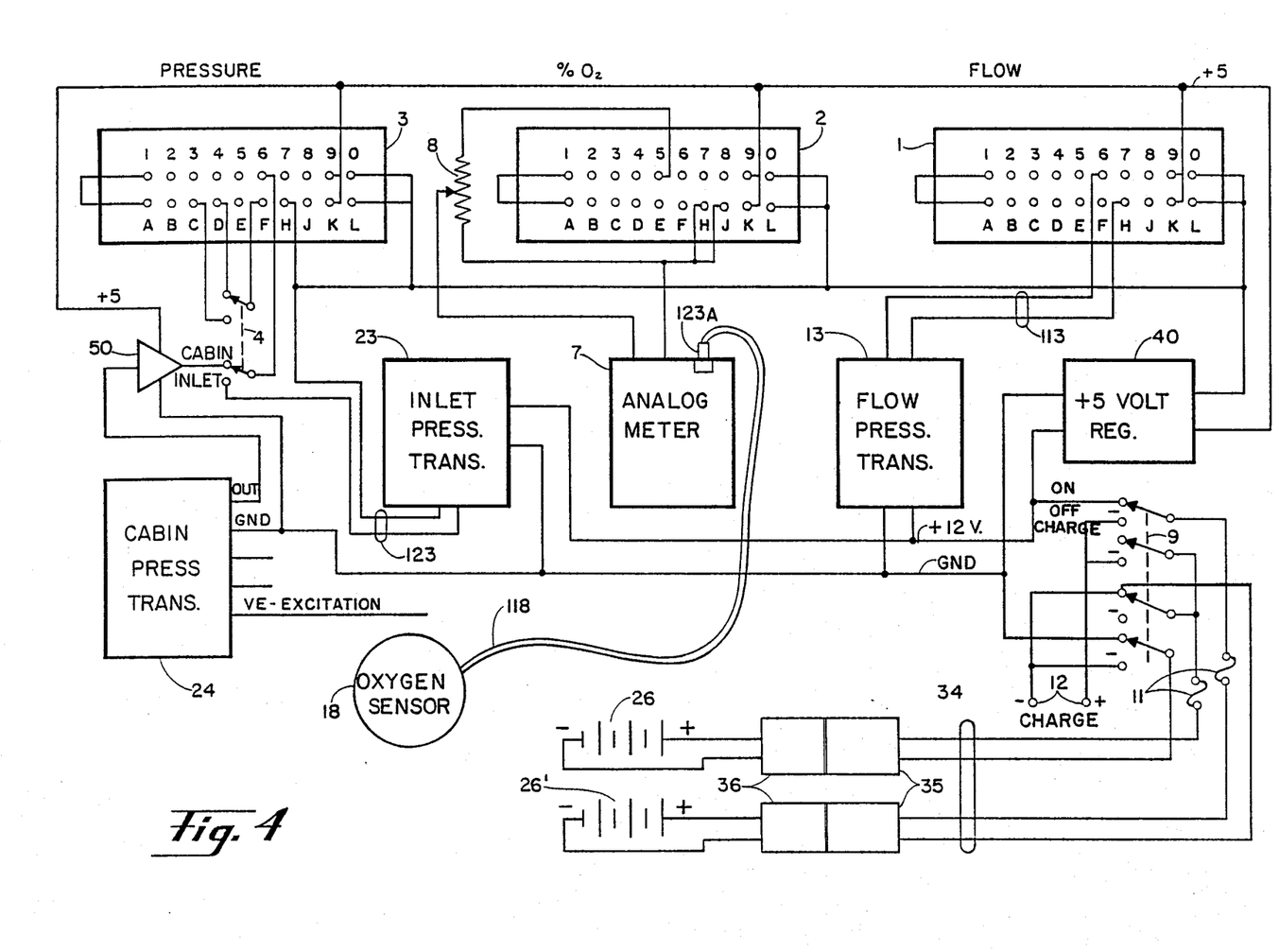
FIG. 4 is a schematic and functional block diagram showing the electrical wiring.

The four variables are monitored on three 3 ½ digit LED direct reading volt meters 1, 2 and 3, shown in FIGS. 1, 2 and 4. The pressures (cabin and outlet) are read from a common meter 3 by utilizing a two-position switch 4 that provides calibrated signals from separate pressure transducers 24 and 23. The flow demand is shown on a second LED meter 1 in liters/minute ATPD (ambient temperature and pressure, dry) as measured with a flow element 16 and differential pressure transducer 13. A third LED meter 2 displays percent oxygen concentration from an oxygen sensor 18 (Rexnord part No. 52032) and an oxygen analyzer and analog meter 7. A small volume flow across the face of the oxygen sensor 18 is necessary for realistic and accurate measurement of oxygen concentration from the MSOGS.

The following list gives the major components used in the analyzer by reference character, with one source and that supplier's part number identified.

formula for correcting for barometric pressure change is:

$$\%O_2 \text{ Reading} \times \frac{\text{calibration pressure}}{\text{cabin pressure}} = \% \text{ actual concentration}$$

Example — For a meter reading of 50% at 10,000 feet (523 mm Hg) and a calibration at ground level (745 mm Hg) of 0– 100%O$_2$ proceed as follows:

$50 \times 745/523 = 71\%$ actual O$_2$ concentration

All variables are hand logged. None of the four variables change rapidly enough for this to be a problem at present. The device as now configured is reliable and simple to operate so there is some reluctance to change it unless a definite need arises. The oxygen concentration and sensor operation were verified in a research chamber by using various known gas mixtures from high pressure cylinders. By checking the analyzer at various altitudes, flows and inlet pressures, it was determined that the sensor was reliable and repeatable as long as the altitude correction factor was used. Small pocket calculators are available for computing the correction factor or a table of values could be formulated for determining the actual percentage of oxygen present in the product breathing gas.

All of the component parts of the USAFSAM portable Oxygen System Analyzer are readily available off-the-shelf items. No new or revolutionary technology is involved in either the design of the device or its construction. The system does configure present day state-of-the-art testing and monitoring equipment into a compact, portable, reliable and flightworthy package to fulfill an operational need. The weight of the analyzer is presently about 31 pounds, but it could easily be reduced by 25% or more. The overall size of the device could be reduced slightly but the necessity to achieve laminar flow does limit the size and shape of the package. The batteries now provide an operational use ex-

| Ref | Item Description | Supplier | Part # | Function |
|---|---|---|---|---|
| 23 | Pressure Transducer 0-50 psig | Validyne | P305D | Measures MSOGS Outlet Pressure |
| 13 | Pressure Transducer 0.08 psid | Validyne | P305D | Measures Pressure Drop of Pneumotach |
| 16 | Flow Element | Fleisch #3 | Pneumotach 6680L528569 | Measures MSOGS Delivery Flows |
| 24 | Transducer 0-60 psia | National Semiconductor | LX1603A | Measures Aircraft Cabin Pressure |
| 1,2,3 | Digital Panel Volt Meter 0-100.0 | Datel | DM-3100N | Provides Digital Readout of Variables |
| 7 | Analog Meter and Oxygen Analyzer | BioMarine | 202R Model A | Regulates Oxygen Sensor Signal to Digital Volt Meter |
| 18 | Oxygen Sensor, Remote 21-100% | Rexnord (Biomarine) | 52032 | Measures Oxygen Concentration |
| 26,26' | Battery, Rechargeable, (gel/Cell) 6 volt | Globe | GC 6120 | Provides 12 Volts to Power System |
| Not shown | Charger, 6 volt | Globe, Johnson Controls | GRC 6450 | Recharges Batteries Between Use |
| 6 | Valve, Control, High Volume | Whitey | B-18VF8 | Regulates Flow |

The cabin pressure readout is necessary to determine the correction factor for all oxygen concentrations since the percent shown on the LED is valid only at ground level (or the elevation where calibrated. The pectancy of 8-10 hours per charge. This time will decrease as the batteries are cycled and recharged many times with use. The system is designed to operate at 12 volts and a minimum voltage of 10.5 is necessary for valid results to be achieved from using the analyzer.

The pressure ranges for the transducers used in this analyzer were chosen because they were on hand and also fit the MSOGS performance parameters. All of the monitoring hardware can be selected to size for other oxygen systems as necessary. This analyzer as presently configured is fairly specific for the B1-B MSOGS but it can be made a general type testing device or be very system specific depending upon the needs of the user.

FIG. 2 shows the parts mounted on the back of the face plate P, including electrical cables which come with the instruments. The other electrical wiring is omitted in FIG. 2 for clarity.

The input connector 5 is coupled via an inlet pressure line 21 to the valve 6. A pressure line 22 is coupled at one end with a fitting 22A to the line 21, and at the other end to the pressure transducer 23. An outlet on the opposite side of the transducer 23, hidden by part 24, is capped so that there is no flow through the transducer. Thus the transducer 23 measures the inlet pressure at connector 5, which is the outlet pressure from the oxygen qeneration system. The pressure is converted to an electrical signal which appears on a conductor (red) of a cable 123 connected to a terminal of the switch 4. A black wire of the cable is connected to common ground.

A pressure transducer 24 (National Semiconductor LX1603A) of a quite different type is provided for measuring the cabin pressure, and is not connected in any way to the line 21. It detects the pressure inside the case 31, and a lead for its output electrical signal is connected to the switch 4. The digital volt meter reads either inlet pressure from transducer 23, or cabin pressure from the transducer 24, depending on the position of switch 4 (see FIG. 1).

Figure 2A:
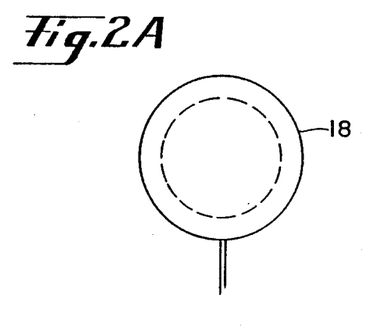
FIGS. 2A, 2B and 2C are top, bottom and side views respectively of the oxygen sensor 18 shown in FIG. 2.
Figure 2B:
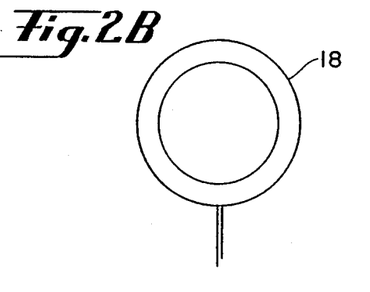
Figure 2C:
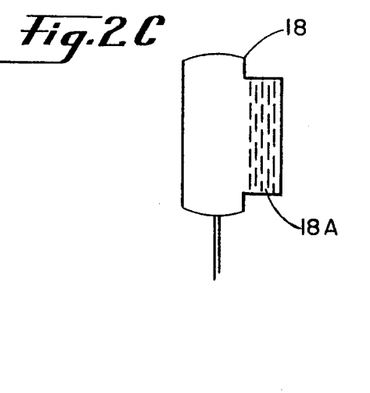
Figure 2D:
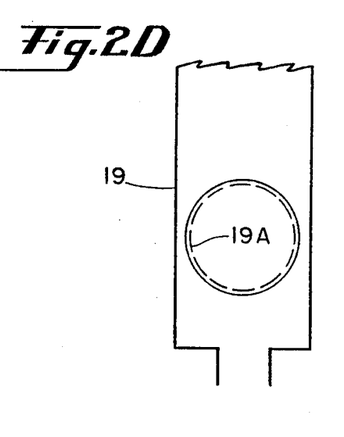
FIG. 2D is a view of the sensor housing 19 shown in FIG. 2.

The flow control valve 6 is coupled via an elbow 20 to a housing 19 for the oxygen sensor 18. FIGS. 2A, 2B and 2C are top, bottom and side views respectively of the oxygen sensor 18; and FIG. 2D is a view of part of the sensor housing 19. The housing 19 has an opening with female threads 19A. The sensor 18 has a projection with male threads 18A which screw into the female housing threads 19A to penetrate the gas stream and provide a gas tight, leak free seal. The outlet of the sensor housing 19 is coupled to a flow tube 17. The output signal of the sensor 18 appears across two conductors in a cable 118, which is wrapped around the flow tube 17 and terminates at a plug 123A, plugqed into a jack 7A. This jack 7A is mounted on a flange 7B of the analog meter 7. This meter 7 provides a 0-100% analog readout of the oxygen concentration, with the portion of the scale between 0 and 20% colored red (see FIG. 1). The analog meter 7 and the digital meter 2 are interconnected, and both indicate the % oxygen.

A flow measurement element 16 is coupled to the oxygen sensor 18 via the flow tube 17, to assure laminar flow. To measure the differential pressure across the flow element 16, its two ends are connected via connector tubes 15 to opposite sides of the pressure transducer 13. The pressure is converted to an electrical signal which appears across two conductors (red and black) of a cable 113 connected to terminals of the meter 1. A flow orifice 33 provides for gas flow from the flow meter 16 to an exit from the case 31. A flow orifice opening/closing lever 30 is shown in FIGS. 1 and 3.

The electrical wiring diagram is shown in FIG. 4. The two batteries 26 and 26' with the connectors 36 are components also shown in FIG. 3. All of the other components of FIG. 4 are mounted on the underside or back of the panel P as shown in FIG. 2. The connectors 36 are shown mated with the connectors 35 to supply power via the four wires 34, with the + leads going to the fuses 11. The power switch 9 is a four-pole three-position switch with no terminal connections for the center OFF position. It is shown in FIG. 4 in the ON position, in which the the batteries 26—26' are connected in series to provide +12 volts for operation of the oxygen system analyzer. In the charge position of switch 9, the batteries 26—26' are connected in parallel via the fuses 11 to the charging receptacles 12. A 6-volt charger (Globe GRC 6450) may be plugged into these receptacles.

The three digital volt meters 1, 2 & 3 are shown as having two rows of ten terminals, one labeled 1-9 & 0, and the other labeled A-F, H, J, K & L. Each of the three meters has a jumper between terminals 1 and A.

A +5-volt regulator 40 and an amplifier 50 shown in FIG. 4 may be mounted on the printed circuit board 25 of FIG. 2. The input of the regulator 40 is connected to the +12 and ground terminals of the power switch 9. A +5-volt output lead is connected to the 9 and K terminals of each of the digital meters 1, 2 & 3, and the another output terminal is the common connection to terminals 0 and L of each of the three meters.

The +12 and ground leads from the power switch 9 are also connected to pressure transducers 13 and 23 to provide input excitation.

The pressure transducer 13, which as shown in FIG. 2 measures flow across the flow measurement element 16, has the two-wire cable 113 connected to terminals 6 and H of the digital meter 1.

The oxygen sensor 18 is connected via the two-wire line 118 (one signal conductor and one ground lead) and jack 123A to the analog meter 7, to provide a readout of oxygen concentration of 0-100%. This analog meter 7 also regulates the oxygen sensor signal to the digital volt meter 2. There is an adjustment potentiometer 8 having a slider terminal connected to the signal lead from the analog meter 7. One end of the potentiometer 8 is connected to terminal 5 of the digital meter 2, and the other end is connected to terminals H & J of the meter 2 and also to the analog meter 7.

The digital meter 3 is used to measure either the oxygen system inlet pressure in one position of the switch 4, or the cabin pressure in the other position. Terminal 6 of the meter 3 is connected via switch 4 when in the inlet position to a signal lead of cable 123 from the pressure transducer 23, or in the cabin position of the switch to the output terminal of the amplifier 50. Terminal H of the meter 3 is connected via switch 4 when in the inlet position to terminal D, or in the cabin position of the switch to terminal C. Termial H of the meter 3 is connected to the common lead from the regulator 40, and also via a lead of cable 123 to the transducer 23. The cabin pressure transducer 24 has an output terminal connected to the input of the amplifier 50. The transducer also has a ground terminal, two terminals which are not used, and a VE-excitation terminal to which +12 volts is connected to excite the bridge.

Figure 5:
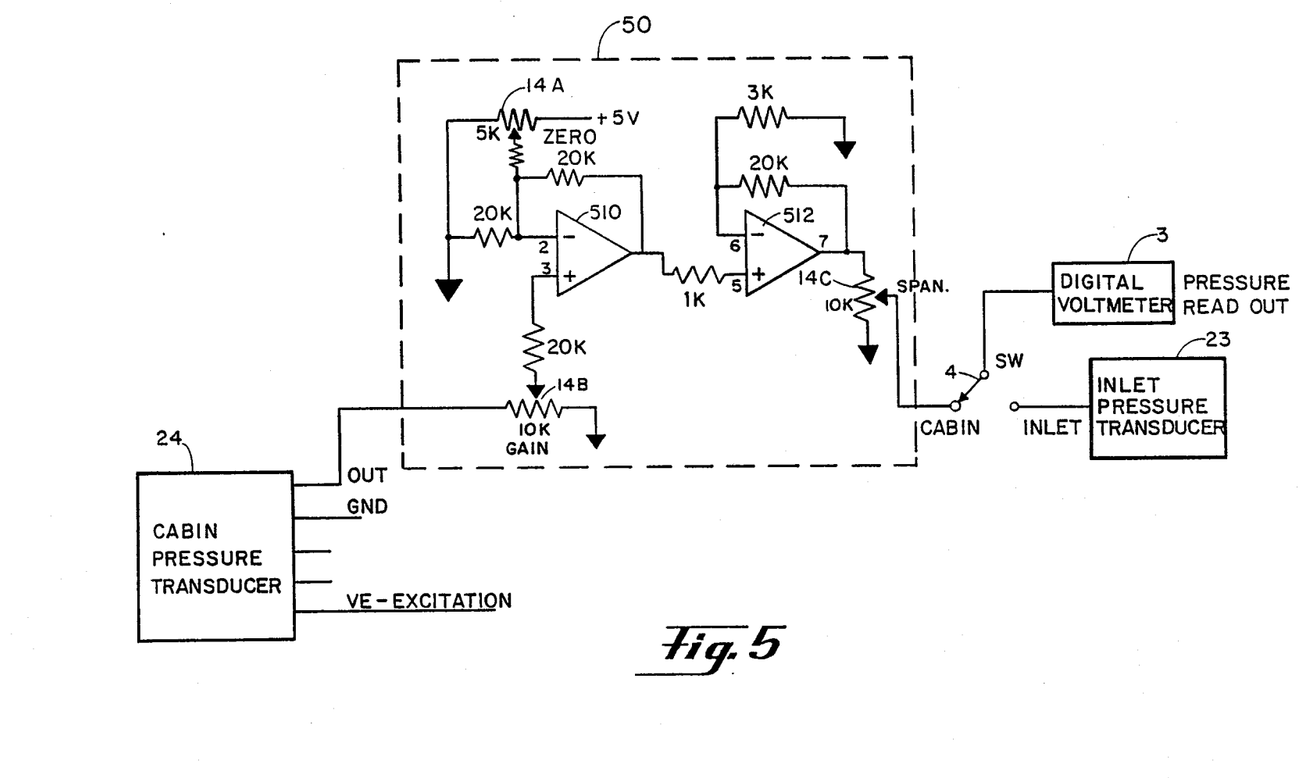
FIG. 5 is a schematic and functional block diagram of the transducer amplifier.

The amplifier 50 is shown in detail in FIG. 5. It comprises two units 510 and 512 of an operational amplifier integrated circuit device type LM324, which has pin 4 at +5 volts and pin 11 at ground. The three potentiometers 14 shown in FIG. 2 on the board 25 are shown in FIG. 5 as potentiometers 14A, 14B and 14C. The potentiometer 14B comprises a 10,000-ohm resistor connected between the signal lead from the cabin pressure transducer 24 and ground, with the sliding tap connected via a 20,000-ohm resistor to the + terminal at pin 3 of the op amp unit 510 for setting input to the amplifier. The potentiometer 14A comprises a 5,000-ohm resistor connected between +5 volts and ground, with the sliding tap connected via a 5,000-ohm resistor to the minus terminal at pin 2 of the op amp unit 510. There are two 20,000-ohm resistors connected to pin 2, one to ground and the other to the output pin 1 of unit 510.

Note in FIG. 2 that the pressure transducers 13 and 23 also have potentiometers 114 and 214 respectively, for zero, center frequency and span. Center frequency is for a factory adjustment with a frequency counter or oscilloscope—not during calibration. Zero and span (sensitivity) control the calibration procedure—setting zero or offset and span or voltage range to adjust the sensitivity and calibrate the transducer. Note that the transducers 13 and 23 have adjustments (zero, center frequency and span) different from the transducer 24.

The output pin 1 of unit 510 is connected via a 1,000-ohm resistor to the + terminal pin 5 of unit 512. The − terminal pin 6 is connected via a 3,000-ohm resistor to ground, and also via a 20,000-ohm resistor to the output pin 7. The potentiometer 14C comprises a 10,000-ohm resistor connected between the output pin 7 and ground, with the sliding tap connected to the "cabin" terminal of one pole of switch 4. As shown more fully in FIG. 4, the digital voltmeter 3 for pressure read out is connected via switch 4 to read either cabin pressure from transducer 24 via amplifier 50, or inlet pressure from transducer 23.

CONCLUSION

The USAFSAM portable Oxygen System Analyzer fulfills an operational need for verification of oxygen delivery system safety and performance requirements for the B1-B MSOGS. So far during the development, fabrication, testing and use of this device it appears to provide a simple and effective solution to preflight and in-flight functional performance checks for OBOGS. As the analyzer is used operationally, discrepancies or use problems may occur, but it is anticipated these will be of a minor nature. Since OBOGS are considered new technology and more and more of the newer aircraft will utilize these types of oxygen systems the need for an analyzer to verify system performance should also markedly increase. The analyzer developed for the MSOGS should be considered a prototype that can be modified or upgraded dependent upon operational constraints or the development of new aircraft oxygen delivery systems.

It is understood that certain modifications to the invention as described may be made, as might occur to one with skill in the field of the invention, within the scope of the appended claims. Therefore, all embodiments contemplated hereunder which achieve the objects of the present invention have not been shown in complete detail. Other embodiments may be developed without departing from the scope of the appended claims.

What is claimed is:

1. An oxygen system analyzer comprising an in-flight test kit for use in a cabin of an aircraft for measuring parameters which comprise breathing gas flow, oxygen concentration and delivery and cabin pressure, for an oxygen system which includes an oxygen system generator installed in the aircraft;

wherein the test kit includes a gas flow passage having coupled together gas inlet means, a flow control valve, an oxygen sensor, a flow tube to assure laminar flow, a flow measurement element, and a flow orifice for gas exit from the test kit, with the gas inlet means having a connector for coupling the test kit to an outlet of the oxygen system generator;

a first pressure transducer coupled via two gas connector tubes across said flow measurement element for measuring pressure drop, an electrical output signal connection from the first pressure transducer to a first digital volt meter for flow readout;

an analog meter having an electrical connection to said oxygen sensor for readout of oxygen concentration, the analog meter being electrically coupled to a second digital volt meter for reading oxygen concentration;

a second pressure transducer coupled via a gas connector tube to said gas inlet means for measuring inlet pressure, a third pressure transducer for measuring cabin pressure, a third digital volt meter for pressure readout, a switch for coupling the third digital voltmeter to either an "inlet" terminal or a "cabin" terminal;

a direct-current power supply means connected for supplying power to the first, second and third pressure transducers, and to the first, second and third digital voltmeters.

2. An oxygen system analyzer according to claim 1, wherein the test kit comprises a portable case having first and second sections;

a panel mounted in the first section, said panel having a front side and a back side; the analog meter and the first, second and third digital volt meters being mounted in openings through the panel with reading faces appearing on the front side; said connector of the gas input means being mounted in an opening of the panel so that connection may be made from the front side; said power switch and flow control valve being mounted in openings through the panel, with each having an operating handle on the front side; an adjustment potentiometer mounted in an opening of the panel electrically connected in the coupling between the second digital volt meter and said switch for aligning the analog meter and the oxygen sensor; the oxygen sensor, flow tube, flow measurement element, and the first, second and third pressure transducers being mounted on the back of the panel;

wherein said second section of the case has an inner side, and said direct-current power supply includes a battery pack mounted therein;

the case being assembled for operation with the first section over the inner side of the second section, and with the front side of the panel facing out.

3. An oxygen system analyzer according to claim 2, further including an amplifier unit as part of said electrical coupling means from the third pressure transducer to the "cabin" terminal;

wherein said direct-current power supply means further includes regulator means for the supply of power to the first, second and third digital voltmeters, the amplifier unit and the regulating means being mounted on a board on the back side of the panel.

4. An oxygen system analyzer according to claim 3, wherein said battery pack comprises two batteries, and wherein said direct-current power supply means further includes two fuse holders mounted in openings in the panel for inserting fuses from the front side, with electrical connections connecting the fuses in series with the batteries, a power switch mounted in an opening in the panel with an operating handle on the front side, and a pair of charging receptacles mounted in openings in the panel for connecting a charger from the front side, the power switch having on, off and charge positions and a plurality of poles, with electrical connections from the power switch to the fuse holders and charge receptacles for connecting the batteries in parallel for charging with the power switch in the charge position, and for connecting the batteries in series with the power switch in the on position for supplying power to the voltage regulator and to the first and second pressure transducers.

* * * * *

UNITED STATES PATENT AND TRADEMARK OFFICE

Certificate

Patent No. 4,765,193                                                                                               Patented: Aug. 23, 1988

On petition requesting issuance of a certificate for correction of inventorship pursuant to 35 USC 256, it has been found that the above-identified patent, through error and without any deceptive intent improperly sets forth the inventorship. Accordingly, it is hereby certified that the correct inventorship of this patent is:

Ronald D. Holden, John B. Tedcor, Andrew O. Beruist, David S. Moran, Mike Eiserer and Thomas A. Naguy.

Signed and Sealed this 12th Day of September 1989.

*Stewart J. Levy*
*Supervisory Patent Examiner*
*Group Art Unit 265*